(12) United States Patent
Tsukamoto et al.

(10) Patent No.: US 10,092,733 B2
(45) Date of Patent: Oct. 9, 2018

(54) BALLOON CATHETER

(71) Applicant: ASAHI INTECC CO., LTD., Nagoya-shi, Aichi (JP)

(72) Inventors: Toshihiko Tsukamoto, Owariasahi (JP); Akihiro Miki, Owariasahi (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 15 days.

(21) Appl. No.: 15/424,384

(22) Filed: Feb. 3, 2017

(65) Prior Publication Data

US 2017/0266420 A1 Sep. 21, 2017

Related U.S. Application Data

(63) Continuation of application No. PCT/JP2016/058198, filed on Mar. 15, 2016.

(51) Int. Cl.
*A61M 25/10* (2013.01)
*A61M 5/00* (2006.01)
*A61M 25/00* (2006.01)
*A61M 25/09* (2006.01)
*A61M 25/01* (2006.01)

(52) U.S. Cl.
CPC ........ *A61M 25/1034* (2013.01); *A61M 5/007* (2013.01); *A61M 25/0023* (2013.01); *A61M 25/09* (2013.01); *A61M 25/10* (2013.01); *A61M 25/1002* (2013.01); *A61M 2025/0186* (2013.01)

(58) Field of Classification Search
CPC ................ A61M 25/10; A61M 3/0295; A61M 2025/1054; A61M 2025/1065; A61M 25/1025; A61M 25/1034; A61M 39/10; A61M 2039/1027; A61M 39/105; A61M 25/0014; A61M 25/1011; A61M 2025/1013; A61B 2017/22054;
(Continued)

(56) References Cited

U.S. PATENT DOCUMENTS 6,723,113 B1 4/2004 Shkolnik
6,982,024 B2 1/2006 Shkolnik
(Continued)

FOREIGN PATENT DOCUMENTS

EP 1 121 955 B1 3/2005
EP 2 918 304 A1 9/2015
(Continued)

*Primary Examiner* — Bhisma Mehta
*Assistant Examiner* — Hong-Van Trinh
(74) *Attorney, Agent, or Firm* — Oliff PLC

(57) ABSTRACT

A balloon catheter has a balloon and an outer shaft fixed to a proximal end of the balloon. Each of the proximal end of the balloon and a distal end of the outer shaft has an inner projection extending in an axial direction of the balloon catheter, an outer projection extending in the axial direction, and a gap formed between the inner projection and the outer projection. At a fixing part, the inner projection of the balloon or the outer projection of the balloon is disposed in the gap of the outer shaft, and the inner projection of the outer shaft or the outer projection of the outer shaft is disposed in the gap of the balloon. The balloon catheter has improved fixing strength between the balloon and the outer shaft without increasing an outer diameter of the fixing part between the balloon and the outer shaft.

11 Claims, 10 Drawing Sheets

(58) Field of Classification Search
CPC .. A61B 2017/22055; A61B 2018/0022; A61B 2018/0025; A61B 2018/00255
See application file for complete search history.

(56) References Cited

U.S. PATENT DOCUMENTS

| | | | |
|---|---|---|---|
| 6,994,687 B1 | 2/2006 | Shkolnik | |
| 7,160,266 B2 | 1/2007 | Shkolnik | |
| 7,179,345 B2 | 2/2007 | Shkolnik | |
| 2014/0172003 A1* | 6/2014 | Goepfrich | A61M 29/02 606/192 |
| 2015/0231375 A1 | 8/2015 | Kubo et al. | |

FOREIGN PATENT DOCUMENTS

| | | |
|---|---|---|
| JP | H01-192369 | 8/1989 |
| JP | H11-128350 | 5/1999 |
| JP | 2001-238957 A | 9/2001 |
| JP | 2009-056297 A | 3/2009 |
| JP | 5237572 | 4/2013 |
| JP | 2015-156880 A | 9/2015 |

* cited by examiner

BALLOON CATHETER

CROSS REFERENCE TO RELATED APPLICATION

This application is a continuation of PCT/JP2016/058198 filed on Mar. 15, 2016, the contents of which are incorporated by reference herein in their entirety.

BACKGROUND

The disclosed embodiments relate to a medical device. Specifically, the disclosed embodiments relate to a balloon catheter.

A balloon catheter expands a constricted portion formed in a blood vessel or a digestive organ to recover a flow of blood or a digestion liquid, and a fixing balloon catheter easily facilitates operation of inserted medical equipment such as a guide wire by expanding a balloon against a blood vessel wall or a digestive organ wall and fixing the balloon. Such balloon catheters mainly include a balloon that is an expansion body, an outer shaft fixed to a proximal end of the balloon, and an inner shaft inserted in the balloon and the outer shaft. Generally, the inner shaft is used to allow a guide wire to pass through the balloon catheter, and an expansion lumen provided between the outer shaft and the inner shaft is used to supply a liquid for expanding the balloon (e.g., contrast medium or physiological saline).

The conventional balloon catheter has a problematically low fixing strength between the proximal end of the balloon and the outer shaft, and the proximal end of the balloon can be removed from a distal end of the outer shaft when the balloon is expanded to expand a constricted portion or to fix the balloon to a blood vessel wall or a digestive organ wall.

As a method of solving this problem, the fixing strength between the balloon and the outer shaft can be improved by coating the outer periphery of the proximal end of the balloon and the distal end of the outer shaft with a heat shrinkable tube that is a separate member (see Japanese Patent Application Laid-open No. 2009-056297, for example). Alternatively, the fixing strength between the balloon and the distal end of the outer shaft can be improved by providing a mutually diagonally cut overlapped part between the proximal end of the balloon and the distal end of the outer shaft (see Japanese Patent No. 5237572, for example).

However, because the heat shrinkable tube is a separate member in the balloon catheter described in Japanese Patent Application Laid-open No. 2009-056297, an outer diameter of the fixing part between the balloon and the outer shaft is large, thereby causing a problem that the passing performance of the balloon catheter is deteriorated. Moreover, in the balloon catheter described in Japanese Patent No. 5237572, there is a limit to how much the fixing area between the balloon and the outer shaft can be increased, which means improvement of the fixing strength between the balloon and the outer shaft also has a limit. Especially when high pressure is imposed on the balloon, there is a risk that the proximal end of the balloon will separate from the distal end of the outer shaft.

SUMMARY

In view of the above-described problems, the disclosed embodiments aim to provide a balloon catheter having improved fixing strength between a balloon and an outer shaft without increasing an outer diameter of a fixing part between the balloon and the outer shaft.

The following means address the above-described problems.

A balloon catheter according to the disclosed embodiments comprises a balloon and an outer shaft fixed to a proximal end of the balloon. Each of the proximal end of the balloon and a distal end of the outer shaft has an inner projection extending in an axis direction, which is in a direction of the longitudinal axis, an outer projection extending in the axis direction, and a gap formed between the inner projection and the outer projection. The inner projection of the balloon or the outer projection of the balloon is disposed in the gap of the outer shaft, and the inner projection of the outer shaft or the outer projection of the outer shaft is disposed in the gap of the balloon. Thus, a fixing area between the balloon and the outer shaft can be easily increased. Therefore, it is possible to improve the fixing strength between the balloon and the outer shaft without increasing an outer diameter at the fixing part between the balloon and the outer shaft. Moreover, the proximal end of the balloon and the distal end of the outer shaft are engaged with each other. Thus, it is possible to reduce the risk that the proximal end of the balloon will separate from the distal end of the outer shaft even when a high pressure is imposed on the balloon.

A bulging portion may be provided at the inner projection of the balloon or the outer projection of the balloon that is disposed in the gap of the outer shaft. This can further expand the fixing area between the balloon and the outer shaft, and the anchoring effect of the bulging portion relative to the gap of the outer shaft can further improve the fixing strength between the balloon and the outer shaft.

Alternatively or additionally, a bulging portion may be provided at the inner projection of the outer shaft or the outer projection of the outer shaft that is disposed in the gap of the balloon. This can further expand the fixing area between the balloon and the outer shaft, and the anchoring effect of the bulging portion relative to the gap of the balloon can further improve the fixing strength between the balloon and the outer shaft.

DETAILED DESCRIPTION OF EMBODIMENTS

Figure 1:
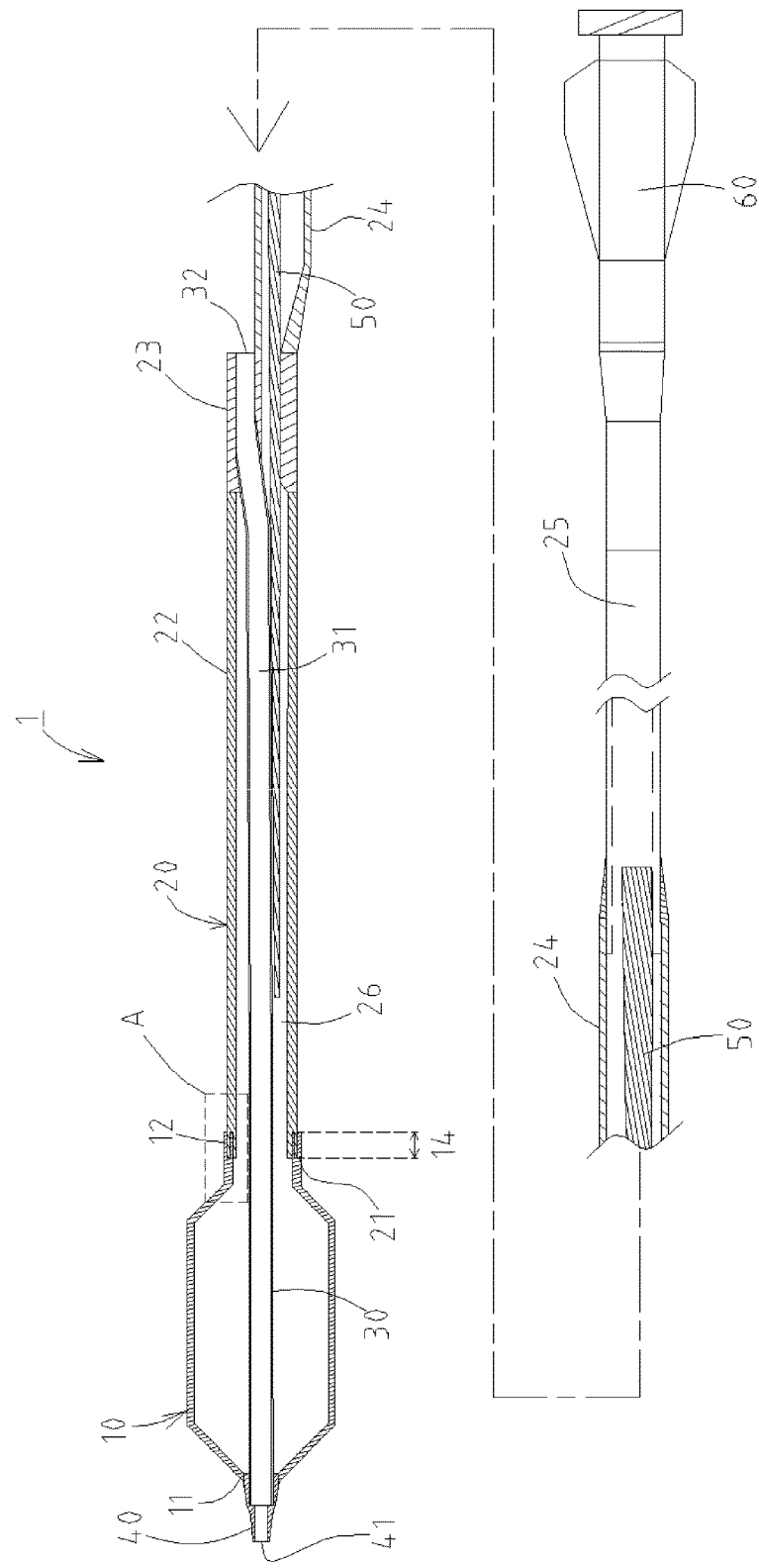
FIG. 1 is a diagram illustrating an entire view of a balloon catheter according to the disclosed embodiments.
Figure 2:
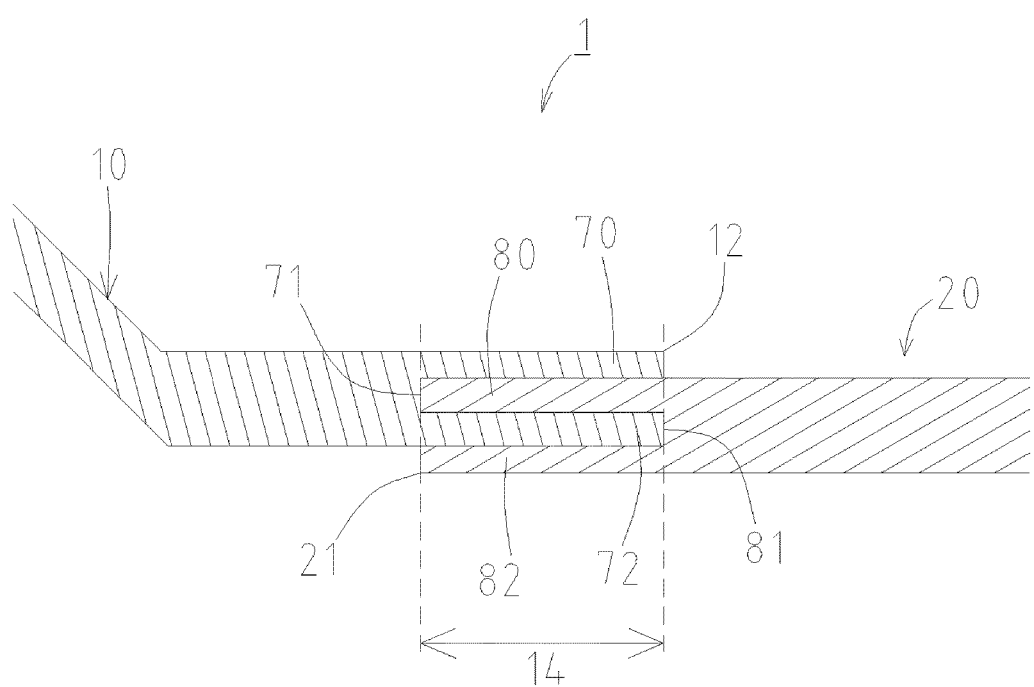
FIG. 2 is an enlarged view of part A of the balloon catheter shown in FIG. 1.
Figure 3A:
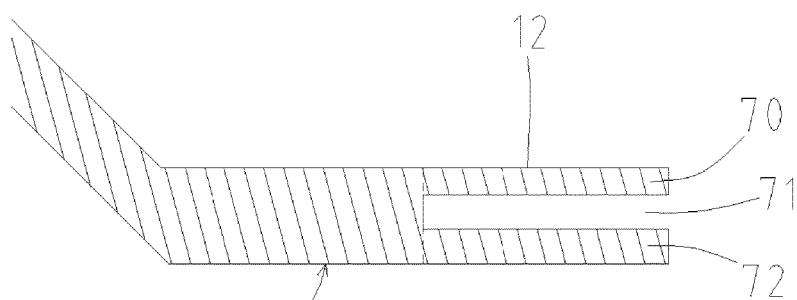
FIGS. 3A and 3B are diagrams illustrating a state where a balloon (FIG. 3A) and an outer shaft (FIG. 3B) that are illustrated in FIG. 2 are separated from each other.
Figure 3B:
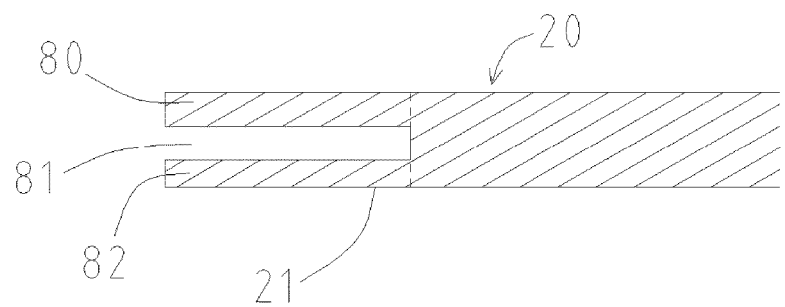

A balloon catheter 1 according to the disclosed embodiments will be described with reference to FIG. 1 to FIG. 3. Throughout the drawings, the left side corresponds to a distal end (front end) to be inserted in a body, while the right side corresponds to a proximal end (rear end) to be operated by a technician such as a physician. FIG. 2 is an enlarged view of part A shown in FIG. 1. FIGS. 3A and 3B are diagrams illustrating, for facilitating understanding, a state where a balloon 10 and an outer shaft 20 that are illustrated in FIG. 2 are separated from each other.

The balloon catheter 1 is, for example, a medical treatment balloon catheter used to expand a constricted portion of a vessel for treatment. As illustrated in FIG. 1, the balloon catheter 1 includes the balloon 10, the outer shaft 20, an inner shaft 30, a distal end tip 40, a reinforcing body 50, and a connector 60.

The balloon 10 for expanding a constricted portion is formed of a resin member, and includes a distal end attachment part 11 at a distal end of the balloon 10, and a proximal end attachment part 12 at a proximal end of the balloon 10. The distal end attachment part 11 is fixed to a distal end of the inner shaft 30 through the distal end tip 40, and the proximal end attachment part 12 is fixed to a distal end 21 of the outer shaft 20. However, the embodiment is not limited thereto. For example, the distal end attachment part 11 may be held between the inner shaft 30 and the distal end tip 40 so that the distal end attachment part 11 of the balloon 10 is directly fixed to the inner shaft 30.

The outer shaft 20 is a tubular member forming an expansion lumen 26 for supplying liquid such as a contrast medium or physiological saline to expand the balloon 10. The outer shaft 20 includes a distal end outer shaft part 22, a guide wire port part 23, an intermediate outer shaft part 24, and a proximal end outer shaft part 25 in this order from the distal end. The distal end outer shaft part 22 and the intermediate outer shaft part 24 are tubes formed of resin of polyamide, polyamide elastomer, polyolefin, polyester, or polyester elastomer. The guide wire port part 23 is a part where the distal end outer shaft part 22, the intermediate outer shaft part 24, and the inner shaft 30 are fixed to one another.

The inner shaft 30 is inserted in the distal end outer shaft part 22, and the above-described expansion lumen 26 is formed between the distal end outer shaft part 22 and the inner shaft 30.

The proximal end outer shaft part 25 is a metallic tubular member: a so-called hypo tube. A distal end of the proximal end outer shaft part 25 is inserted into and fixed to a proximal end of the intermediate outer shaft part 24. A connector 60 is attached to a proximal end of the proximal end outer shaft part 25. When liquid such as a contrast medium or physiological saline for expanding the balloon 10 is supplied from an indeflator (not illustrated) that can be attached to the connector 60, the liquid passes through the expansion lumen 26 and expands the balloon 10. Note that the material of the proximal end outer shaft part 25 is not particularly limited, and stainless steel (SUS302, SUS304) or a superelastic alloy such as a Ni—Ti alloy can be used.

The inner shaft 30 has therein a guide wire lumen 31 into which a guide wire can be inserted. A proximal end of the inner shaft 30 is fixed to the guide wire port part 23 of the outer shaft 20 to form a proximal end guide wire port 32. A technician can exchange guide wires through the proximal end guide wire port 32.

As described later, the distal end tip 40 is fixed to a distal end of the inner shaft 30. The distal end tip 40 is formed of flexible resin. The material is not particularly limited, and polyurethane, polyurethane elastomer, and the like can be used. Moreover, the distal end tip 40 has a distal end guide wire port 41 on its distal end.

The reinforcing body 50 is attached on an inner periphery of the distal end of the proximal end outer shaft part 25. The reinforcing body 50 has a circular cross section, and is a metal wire tapered toward the distal end. The material of the reinforcing body 50 is not particularly limited, and stainless steel (SUS304) or a superelastic alloy such as a Ni—Ti alloy can be used. The reinforcing body 50 extends through the intermediate outer shaft part 24 and past the guide wire port part 23 and into to the distal end outer shaft part 22.

As illustrated in FIG. 3A, there are provided, at the proximal end 12 of the balloon 10, an outer projection 70 extending in an axis direction (an axial direction of the balloon catheter 1), an inner projection 72 extending in the axis direction, and a gap 71 formed between the outer projection 70 and the inner projection 72. That is, the outer projection 70 and the inner projection 72 are spaced apart from each other. As illustrated in FIG. 3B, there are provided, at the distal end 21 of the outer shaft 20, an outer projection 80 extending in the axis direction, an inner projection 82 extending in the axis direction, and a gap 81 formed between the outer projection 80 and the inner projection 82.

In the balloon catheter 1, the inner projection 72 of the balloon 10 is disposed in the gap 81 of the outer shaft 20, and the outer projection 80 of the outer shaft 20 is disposed in the gap 71 of the balloon 10 (see FIG. 2). In other words, at a fixing part 14 between the proximal end 12 of the balloon 10 and the distal end 21 of the outer shaft 20, there are sequentially laminated in a diameter direction (in a radial direction from an inside of the balloon catheter 1 toward an outside of the balloon catheter 1) the inner projection 82 of the outer shaft 20, the inner projection 72 of the balloon 10, the outer projection 80 of the outer shaft 20, and the outer projection 70 of the balloon 10.

In this manner, the proximal end 12 of the balloon 10 and the distal end 21 of the outer shaft 20 are engaged with each other, whereby a fixing area (the contact area at the fixing part 14) between the balloon 10 and the outer shaft 20 can be easily increased. Thus, it is possible to improve the fixing strength between the balloon 10 and the outer shaft 20 without increasing an outer diameter at the fixing part 14 between the balloon 10 and the outer shaft 20. As a result, it is possible to reduce the risk that the proximal end 12 of the balloon 12 will separate from the distal end 21 of the outer shaft 20 even when a technician imposes high pressure on the balloon 10.

Figure 4:
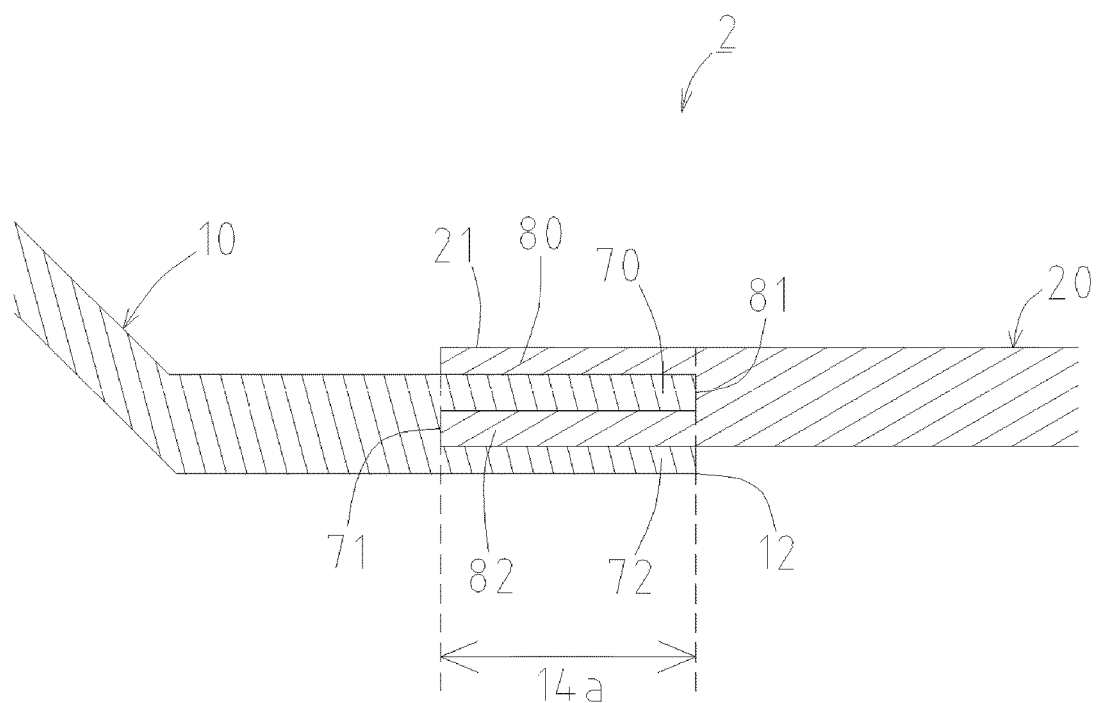
FIG. 4 is a diagram illustrating a part of a balloon catheter according to the disclosed embodiments.

Next, a balloon catheter 2 of the disclosed embodiments will be described with reference to FIG. 4. Explaining only a difference from the balloon catheter 1, in the balloon catheter 2, the outer projection 70 of the balloon 10 is disposed in the gap 81 of the outer shaft 20, and the inner projection 82 of the outer shaft 20 is disposed in the gap 71 of the balloon 10 (see FIG. 4). In other words, at a fixing part 14a between the proximal end 12 of the balloon 10 and the distal end 21 of the outer shaft 20, there are sequentially laminated in the diameter direction the inner projection 72 of the balloon 10, the inner projection 82 of the outer shaft 20, the outer projection 70 of the balloon 10, and the outer projection 80 of the outer shaft 20.

The fixing part 14a of the balloon catheter 2 has a structure in which the proximal end 12 of the balloon 10 and the distal end 21 of the outer shaft 20 are engaged with each other, similarly to the fixing part 14 of the balloon catheter 1. Thus, a fixing area between the balloon 10 and the outer shaft 20 can be easily increased. Thus, it is possible to improve the fixing strength between the balloon 10 and the outer shaft 20 without increasing an outer diameter at the fixing part 14a between the balloon 10 and the outer shaft 20. As a result, it is possible to reduce the risk that the proximal end 12 of the balloon 10 will separate from the distal end 21 of the outer shaft 20 even when a technician imposes a high pressure on the balloon 10.

Figure 5A:
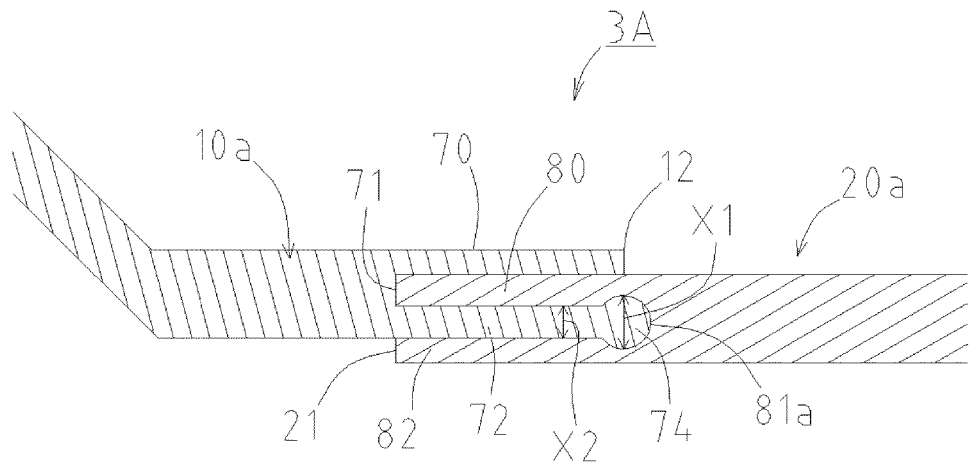
FIGS. 5A and 5B are diagrams illustrating parts of balloon catheters according to the disclosed embodiments.

Next, balloon catheters 3A, 3B of the disclosed embodiments will be described with reference to FIG. 5A and FIG. 5B. Explaining only a difference from the balloon catheter 1, in the balloon catheter 3A, a bulging portion 74 is provided at a proximal end of the inner projection 72 of a balloon 10a disposed in a gap 81a of an outer shaft 20a, as illustrated in FIG. 5A. The bulging portion 74 is formed of the same material as the inner projection 72, and has a greater thickness in the diameter direction than the inner projection 72. In other words, a thickness X1 of the bulging portion 74 is larger than a thickness X2 of the inner projection 72 (X1>X2).

Figure 5B:
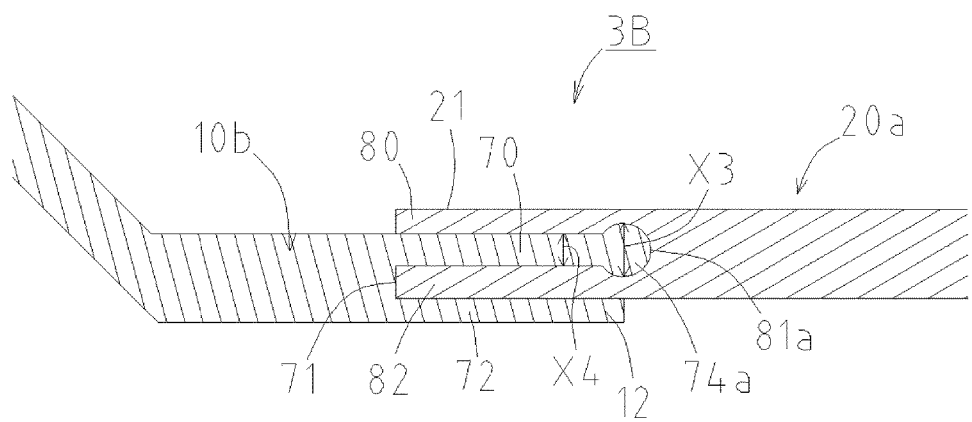

Similarly, explaining only a difference from the balloon catheter 2, in the balloon catheter 3B, a bulging portion 74a is provided at a proximal end of the outer projection 70 of a balloon 10b disposed in the gap 81a of the outer shaft 20a, as illustrated in FIG. 5B. The bulging portion 74a is formed of the same material as the outer projection 70, and has a greater thickness in the diameter direction than the outer projection 70. In other words, a thickness X3 of the bulging portion 74a is larger than a thickness X4 of the outer projection 70 (X3>X4).

In this manner, the bulging portion 74, 74a provided at the proximal end of the inner projection 72 or the outer projection 70 is disposed in the gap 81a of the outer shaft 20a, whereby a fixing area between the balloons 10a, 10b and the outer shaft 20a can be further increased, and the anchoring effect of the bulging portion 74, 74a relative to the gap 81a of the outer shaft 20a can further improve the fixing strength between the balloon 10a, 10b and the outer shaft 20a.

Figure 6A:
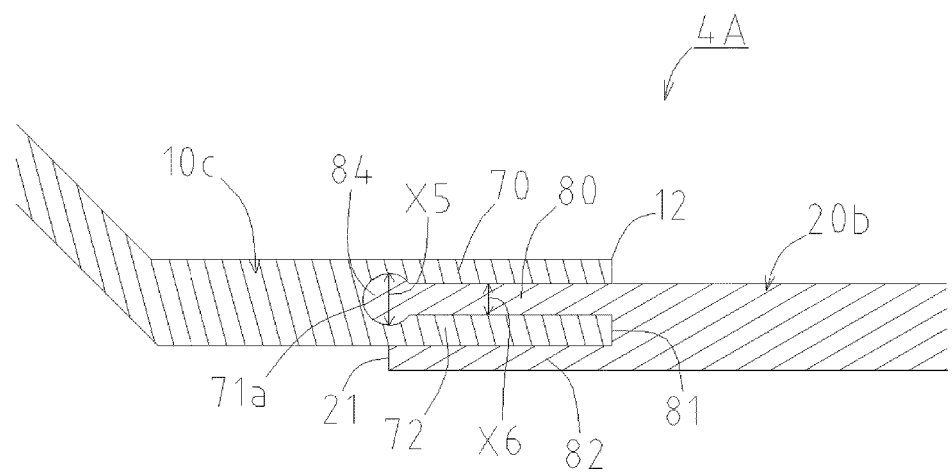
FIGS. 6A and 6B are diagrams illustrating parts of balloon catheters according to the disclosed embodiments.

Next, balloon catheters 4A, 4B of the disclosed embodiments will be described with reference to FIG. 6A and FIG. 6B. Explaining only a difference from the balloon catheter 1, in the balloon catheter 4A, a bulging portion 84 is provided at a distal end of the outer projection 80 of an outer shaft 20b disposed in a gap 71a of a balloon 10c, as illustrated in FIG. 6A. The bulging portion 84 is formed of the same material as the outer projection 80, and has a greater thickness in the diameter direction than the outer projection 80. In other words, a thickness X5 of the bulging portion 84 is larger than a thickness X6 of the outer projection 80 (X5>X6).

Figure 6B:
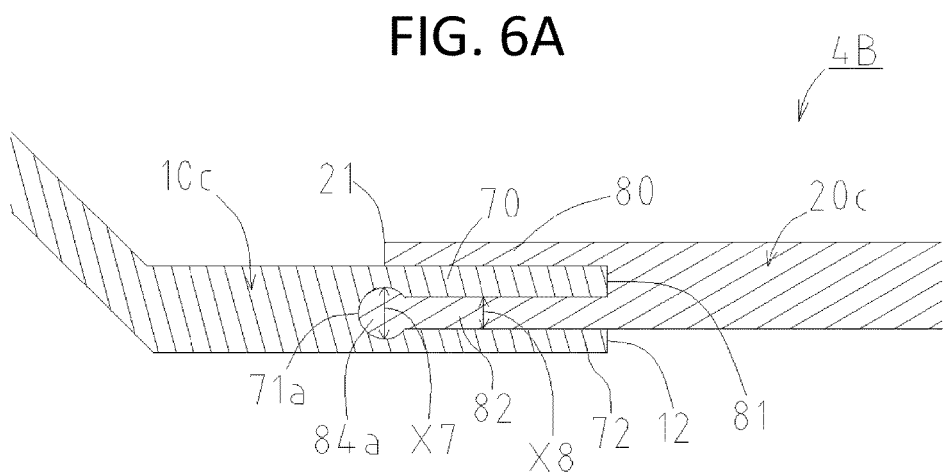

Similarly, explaining only a difference from the balloon catheter 2, in the balloon catheter 4B, a bulging portion 84a is provided at a distal end of the inner projection 82 of an outer shaft 20c disposed in the gap 71a of the balloon 10c, as illustrated in FIG. 6B. The bulging portion 84a is formed of the same material as the inner projection 82, and is has a greater thickness in the diameter direction than the inner projection 82. In other words, a thickness X7 of the bulging portion 84a is larger than a thickness X8 of the inner projection 82 (X7>X8).

In this manner, the bulging portion 84, 84a provided at the distal end of the outer projection 80 or the inner projection 82 is disposed in the gap 71a of the balloon 10c, whereby the fixing area between the balloon 10c and the outer shaft 20b, 20c can be further increased, and the anchoring effect of the bulging portion 84, 84a relative to the gap 71a of the balloon 10c can further improve the fixing strength between the balloon 10c and the outer shaft 20b, 20c.

Figure 7A:
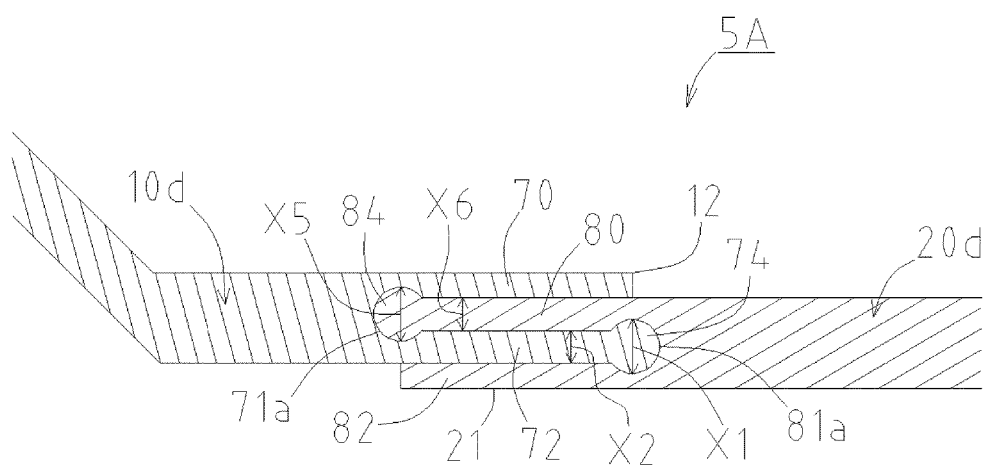
FIGS. 7A and 7B are diagrams illustrating parts of balloon catheters according to the disclosed embodiments.

Next, balloon catheters 5A, 5B of the disclosed embodiments will be described with reference to FIG. 7A and FIG. 7B. Explaining only a difference from the balloon catheter 4A, in the balloon catheter 5A, the bulging portion 74 is provided, in addition to the bulging portion 84, at the proximal end of the inner projection 72 of a balloon 10d disposed in the gap 81a of an outer shaft 20d, as illustrated in FIG. 7A. Note that the bulging portion 74 is same as in the balloon catheter 3A shown in FIG. 5A, and thus the explanation thereof is omitted.

Figure 7B:
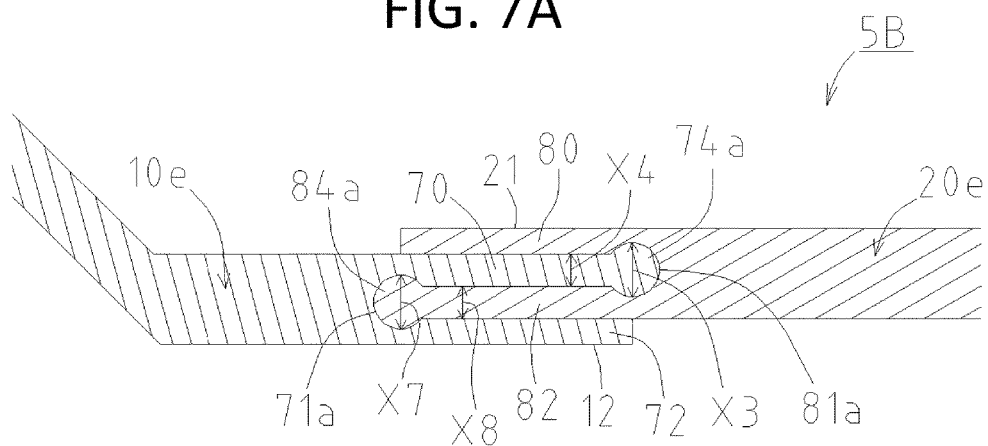

Similarly, explaining only a difference from the balloon catheter 4B, in the balloon catheter 5B, the bulging portion 74a is provided, in addition to the bulging portion 84a, at the proximal end of the outer projection 70 of a balloon 10e disposed in the gap 81a of an outer shaft 20e, as illustrated in FIG. 7B. Note that the bulging portion 74a is same as in the balloon catheter 3B shown in FIG. 5B, and thus the explanation thereof is omitted.

In this manner, the bulging portion 84, 84a provided at the distal end of the outer projection 80 or the inner projection 82 is disposed in the gap 71a of the balloon 10d, 10e, and the bulging portion 74, 74a provided at the proximal end of the inner projection 72 or the outer projection 70 is disposed in the gap 81a of the outer shaft 20d, 20e, whereby the fixing area between the balloon 10d, 10e and the outer shaft 20d, 20e can be further increased. In addition, the anchoring effect of the bulging portion 84, 84a relative to the gap 71a of the balloon 10d, 10e, and the anchoring effect of the bulging portion 74, 74a relative to the gap 81a of the outer shaft 20d, 20e can further improve the fixing strength between the balloon 10d, 10e and the outer shaft 20d, 20e.

Figure 8A:
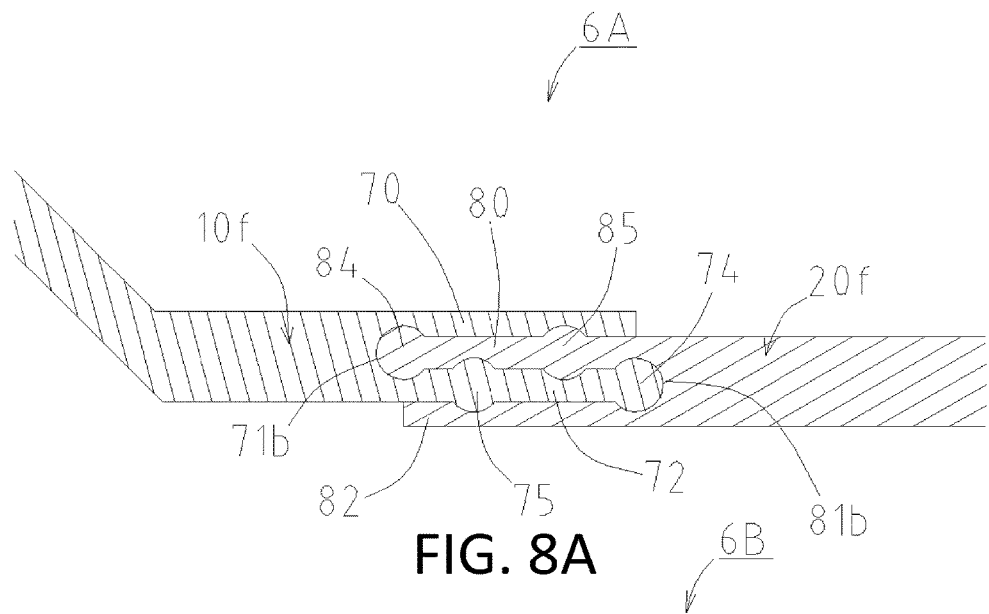
FIGS. 8A and 8B are diagrams illustrating parts of balloon catheters according to the disclosed embodiments.
Figure 8B:
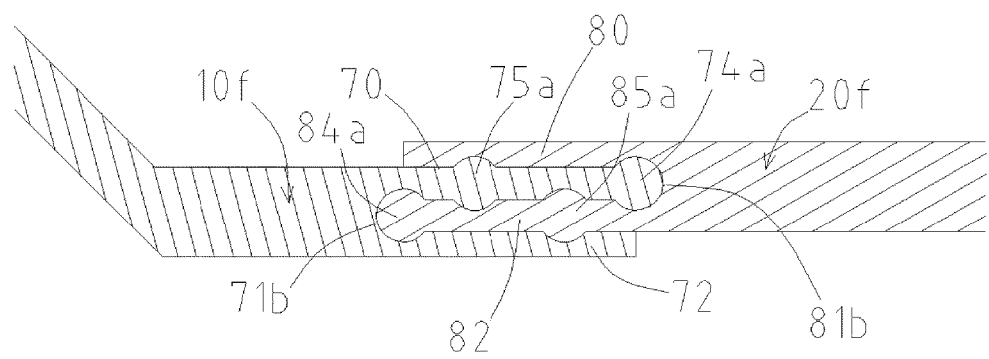

The balloon catheters 3A to 5B include one bulging portion 74 at the proximal end of the inner projection 72 of the balloon 10a, 10d (catheter 3A, 5A), one bulging portion 74a at the proximal end of the outer projection 70 of the balloon 10b, 10e (catheter 3B, 5B), one bulging portion 84 at the distal end of the outer projection 80 of the outer shaft 20b, 20d (catheter 4A, 5A), and one bulging portion 84a at the distal end of the inner projection 82 of the outer shaft 20c, 20e (catheter 4B, 5B). The number and the position of the bulging portions 74, 74a, 84, 84a are not particularly limited. For example, in a balloon catheter 6A of the disclosed embodiments illustrated in FIG. 8A, two bulging portions 84, 85 provided at the distal end and the middle (an intermediate position) of the outer projection 80 of an outer shaft 20f may be disposed in a gap 71b of a balloon 10f, and two bulging portions 74, 75 provided at the proximal end and the middle of the inner projection 72 of the balloon 10f may be disposed in a gap 81b of the outer shaft 20f. Moreover, in the balloon catheter 6B of the disclosed embodiments illustrated in FIG. 8B, two bulging portions 84a, 85a provided at the distal end and the middle of the inner projection 82 of the outer shaft 20f may be disposed in the gap 71b of the balloon 10f, and two bulging portions 74a, 75a provided at the proximal end and the middle of the outer projection 70 of the balloon 10f may be disposed in the gap 81b of the outer shaft 20f.

Note that the form of the bulging portions 74, 74*a*, 75, 75*a*, 84, 84*a*, 85, 85*a* is not limited to the form illustrated in FIG. 5A to FIG. 8B as long as the anchoring effect can be obtained.

Figure 9A:
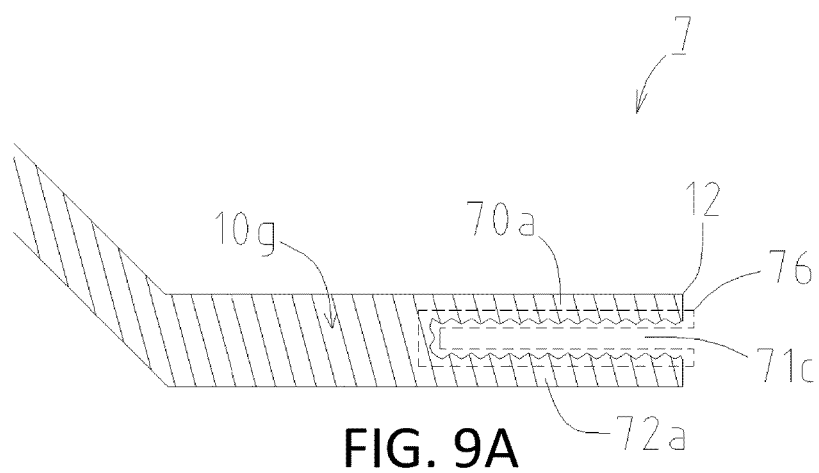
FIGS. 9A and 9B are diagrams illustrating a state where a balloon (FIG. 9A) and an outer shaft (FIG. 9B) are separated from each other.
Figure 9B:
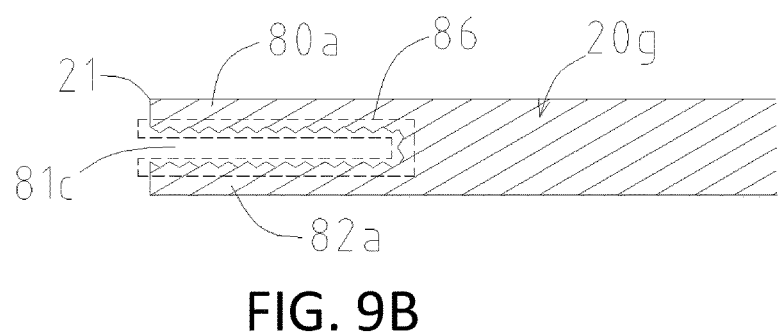

Instead of the above-described bulging portions 74, 74*a*, 75, 75*a*, 84, 84*a*, 85, 85*a*, an uneven inner peripheral surface 76 may be provided in a gap 71*c* of a balloon 10*g*, and an uneven inner peripheral surface 86 may be provided in a gap 81*c* of an outer shaft 20*g*, as illustrated in a balloon catheter 7 shown in FIGS. 9A, 9B.

To be more specific, there are provided, at the proximal end 12 of the balloon 10*g*, an outer projection 70*a* extending in the axis direction, an inner projection 72*a* extending in the axis direction, and the gap 71*c* that is formed between the outer projection 70*a* and the inner projection 72*a* and that has the uneven inner peripheral surface 76, as illustrated in FIG. 9A. Moreover, as illustrated in FIG. 9B, there are provided, at the distal end 21 of the outer shaft 20*g*, an outer projection 80*a* extending in the axis direction, an inner projection 82*a* extending in the axis direction, and the gap 81*c* that is formed between the outer projection 80*a* and the inner projection 82*a* and that has the uneven inner peripheral surface 86. Similarly to FIGS. 3A, 3B, FIGS. 9A, 9B illustrate, for facilitating understanding, the state where the balloon 10*g* and the outer shaft 20*g* are separated from each other.

In such a manner, the inner peripheral surface 76 is provided in the gap 71*c* of the balloon 10*g*, and the inner peripheral surface 86 is provided in the gap 81*c* of the outer shaft 20*g*. Then, the inner peripheral surface 76 and the inner peripheral surface 86 are fixed to each other, whereby the fixing area between the balloon 10*g* and the outer shaft 20*g* can be increased. As a result, it is possible to improve the fixing strength between the balloon 10*g* and the outer shaft 20*g*.

Next, a balloon catheter 8 of the disclosed embodiments will be described with reference to FIG. 10. In the balloon catheter 8, the same symbols as in the balloon catheters 1 to 7 described above represent the same members unless otherwise specified.

The balloon catheter 8 is, for example, a fixing balloon catheter that facilitates insertion of medical equipment such as a guide wire by expanding a balloon against a blood vessel wall or a digestive organ wall and fixing the balloon. As illustrated in FIG. 10, the balloon catheter 8 includes the balloon 10, the outer shaft 20, a first inner shaft 34, a second inner shaft 33, the reinforcing body 50, and a connector 62.

In the outer shaft 20, the second inner shaft 33 extends throughout the whole length of the balloon catheter 8. A guide wire can be inserted into the second inner shaft 33. In order to facilitate insertion of the guide wire, the connector 62 is connected to the proximal end of the outer shaft 20 and a proximal end of the second inner shaft 33. A first distal end port 33*a* is provided at a distal end of the second inner shaft 33, and a first insertion port 64 is provided at the proximal end of the second inner shaft 33 through the connector 62.

In the outer shaft 20, the first inner shaft 34 extends, in parallel to the second inner shaft 33, from the middle to a distal end of the balloon catheter 8. Similarly to the second inner shaft 33, the guide wire can be inserted into the first inner shaft 34. A second distal end port 34*a* is provided at a distal end of the first inner shaft 34, and a second insertion port 34*b* is provided at a proximal end of the first inner shaft 34.

The outer shaft 20, the first inner shaft 34, and the second inner shaft 33 are formed of thermoplastic resin. For example, polyamide, polyamide elastomer, polyolefin, polyester, polyester elastomer, or nylon can be used.

The second inner shaft 33 extends over the whole length of the balloon catheter 8. Thus, it can be difficult for the technician to change the guide wire inserted in the second inner shaft 33 because the second inner shaft 33 is long. However, the guide wire inserted in the second inner shaft 33 improves rigidity of the balloon catheter 8, and thus the technician can easily push the balloon catheter 8 in the distal direction.

Moreover, the first inner shaft 34 extends only from the middle to the distal end of the balloon catheter 8. Thus, the technician can easily change the guide wire inserted in the first inner shaft 34. However, the rigidity of the balloon catheter 8 is improved only from the middle to the distal end of the balloon catheter 8 where the guide wire is inserted, and the balloon catheter 8 can break around the second insertion port 34*b* of the first inner shaft 34 where the rigidity changes suddenly when the technician pushes the balloon catheter 8 in the distal direction.

By including both the first inner shaft 34 and the second inner shaft 33, the technician can rapidly change a second guide wire inserted in the first inner shaft 34 while a first guide wire is inserted in the second inner shaft 33, and the balloon catheter 8 can be easily pushed in the distal direction.

Figure 10:
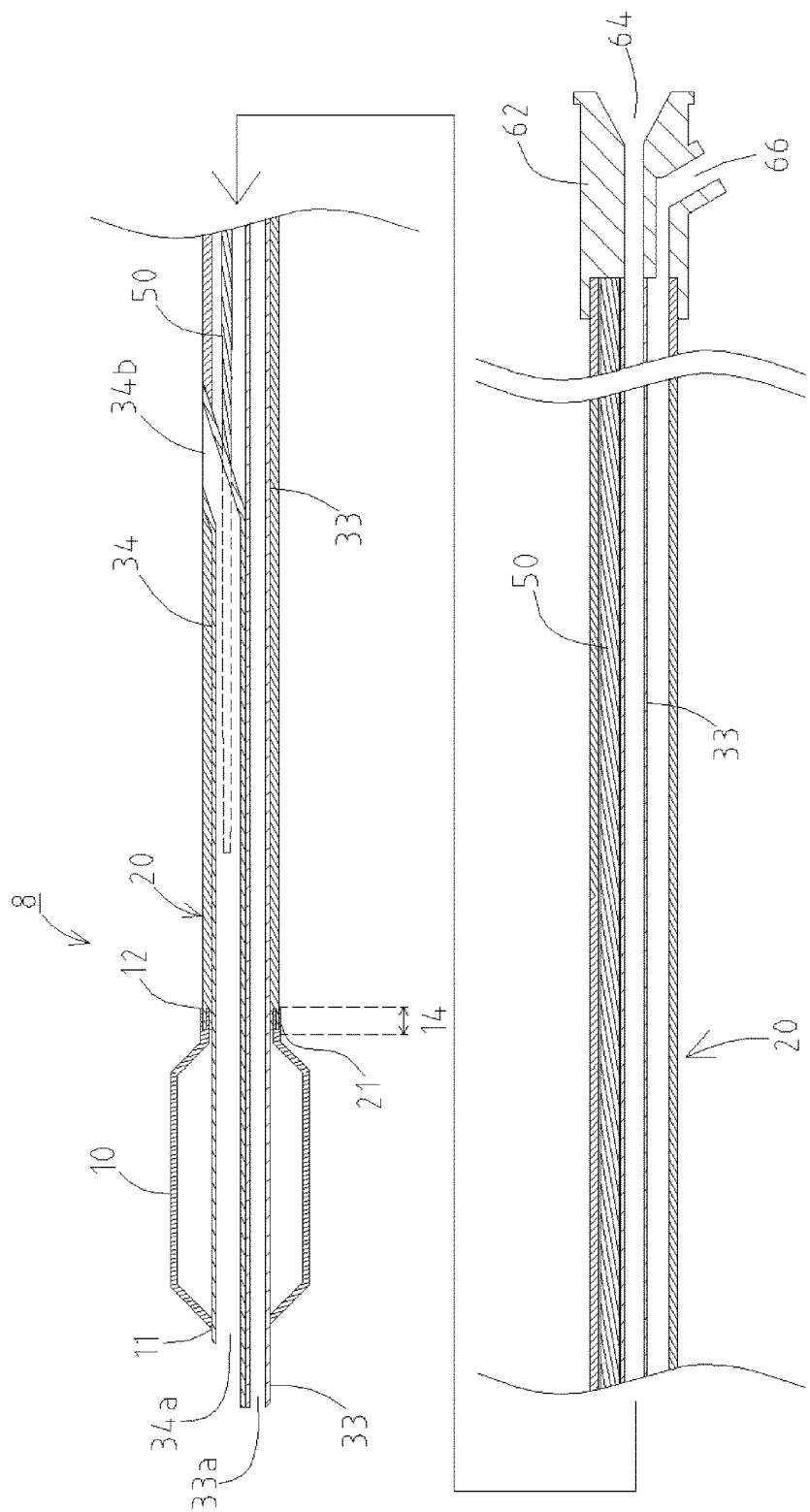
FIG. 10 is a diagram illustrating an entire view of a balloon catheter according to the disclosed embodiments.

As illustrated in FIG. 10, the balloon 10 fixed to a blood vessel wall or a digestive organ wall is formed of a resin member, and includes the distal end attachment part 11 at the distal end of the balloon 10, and the proximal end attachment part 12 at the proximal end of the balloon 10. The distal end attachment part 11 is fixed to the first inner shaft 34 and the second inner shaft 33, while the proximal end attachment part 12 is fixed to the distal end 21 of the outer shaft 20.

In order to expand the balloon 10, an expansion lumen for supplying liquid such as a contrast medium or physiological saline is provided between the outer shaft 20, and the first inner shaft 34 and the second inner shaft 33, although it is not illustrated. A liquid supply port 66 to which an indeflator (not illustrated) can be attached is provided in the connector 62. The liquid such as a contrast medium or physiological saline supplied from the liquid supply port 66 passes through the expansion lumen to the balloon 10, then expanding the balloon 10.

In the balloon catheter 8, the metal reinforcing body 50 extending in an axis direction is inserted between the outer shaft 20 and the second inner shaft 33. The distal end of the reinforcing body 50 extends past the second insertion port 34*b* of the first inner shaft 34 in the distal direction.

Similarly to the balloon catheters 1 to 7, in the balloon catheter 8, the proximal end 12 of the balloon 10 and the distal end 21 of the outer shaft 20 are engaged with each other, whereby a fixing area between the balloon 10 and the outer shaft 20 can be easily increased. Thus, it is possible to improve the fixing strength between the balloon 10 and the outer shaft 20 without increasing an outer diameter at the fixing part 14 between the balloon 10 and the outer shaft 20. As a result, even when a technician imposes a high pressure on the balloon 10, it is possible to reduce the risk that the proximal end 12 of the balloon 10 will separate from the distal end 21 of the outer shaft 20.

What is claimed is:

1. A balloon catheter comprising:
    a balloon, a proximal end of the balloon having an inner projection extending in an axial direction of the balloon catheter, an outer projection extending in the axial direction, and a gap extending in the axial direction along an entire length of the inner and outer projections of the balloon; and an outer shaft fixed to the proximal end of the balloon, a distal end of the outer shaft having an inner projection extending in the axial direction, an outer projection extending in the axial direction, and a gap extending in the axial direction along an entire length of the inner and outer projections of the outer shaft, wherein either:

the inner projection of the balloon is disposed in the gap of the outer shaft, and the outer projection of the outer shaft is disposed in the gap of the balloon;

or the outer projection of the balloon is disposed in the gap of the outer shaft, and the inner projection of the outer shaft is disposed in the gap of the balloon.

2. The balloon catheter according to claim 1, wherein:

the inner projection of the balloon is disposed in the gap of the outer shaft; and the outer projection of the outer shaft is disposed in the gap of the balloon.

3. The balloon catheter according to claim 1, wherein:

the outer projection of the balloon is disposed in the gap of the outer shaft; and the inner projection of the outer shaft is disposed in the gap of the balloon.

4. The balloon catheter according to claim 1, wherein a bulging portion is provided at the inner projection of the balloon or the outer projection of the balloon that is disposed in the gap of the outer shaft.

5. The balloon catheter according to claim 4, wherein the bulging portion is provided at a distal end of the inner projection of the balloon or a distal end of the outer projection of the balloon that is disposed in the gap of the outer shaft.

6. The balloon catheter according to claim 4, wherein more than one bulging portion is provided at the inner projection of the balloon or the outer projection of the balloon that is disposed in the gap of the outer shaft.

7. The balloon catheter according to claim 4, wherein a bulging portion is provided at the inner projection of the outer shaft or the outer projection of the outer shaft that is disposed in the gap of the balloon.

8. The balloon catheter according to claim 1, wherein a bulging portion is provided at the inner projection of the outer shaft or the outer projection of the outer shaft that is disposed in the gap of the balloon.

9. The balloon catheter according to claim 8, wherein the bulging portion is provided at a distal end of the inner projection of the outer shaft or a distal end of the outer projection of the outer shaft that is disposed in the gap of the balloon.

10. The balloon catheter according to claim 8, wherein more than one bulging portion is provided at the inner projection of the outer shaft or the outer projection of the outer shaft that is disposed in the gap of the balloon.

11. The balloon catheter according to claim 1, wherein:

the gap of the balloon has an uneven inner peripheral surface, which is provided in the gap of the outer shaft; and the gap of the outer shaft has an uneven inner peripheral surface, which is provided in the gap of the balloon.

* * * * *